United States Patent [19]

Wildonger

[11] 4,227,004

[45] Oct. 7, 1980

[54] SYNTHESIS OF SUBSTITUTED 1-ARALKYL-1H-v-TRIAZOLES

[75] Inventor: Richard A. Wildonger, Newark, Del.

[73] Assignee: ICI Americas Inc., Wilmington, Del.

[21] Appl. No.: 450

[22] Filed: Jan. 2, 1979

[51] Int. Cl.³ .......................................... C07D 249/04
[52] U.S. Cl. ..................................................... 548/255
[58] Field of Search ..................... 260/308 A; 548/255

[56] References Cited

U.S. PATENT DOCUMENTS 3,985,765  10/1976  Buckler et al. ................. 260/308 A

FOREIGN PATENT DOCUMENTS 754501  8/1970  Belgium .
754506  8/1970  Belgium .
1940628  2/1971  Fed. Rep. of Germany .
2407302  8/1975  Fed. Rep. of Germany .

OTHER PUBLICATIONS

March, "Advanced Organic Chemistry: Reactions, Mechanisms and Structures", 1968, p. 357.
Katritzky et al., "Advances in Heterocyclic Chemistry", vol. 16, 1974, p. 421.
Raap, "Canadian Jorn. Chem.", vol. 49, 1971, pp. 1792–1798.
Miller, "Tetrahedron Letters", No. 34, 1975, pp., 2959–2960.
Morrison et al., *Organic Chemistry*, 2nd Ed., 1966, Allyn and Bacon, Inc., Boston, pp. 382–383; 592–593; 911–913.

*Primary Examiner*—Donald G. Daus
*Assistant Examiner*—James H. Turnipseed

[57] ABSTRACT

Substituted 1-aralkyl-1H-v-triazoles are prepared from a suitable 1-aralkyl-1H-v-triazole by a process comprising an alkylation step and dependent on the product desired suitably followed by an oxidation step and decarboxylation step.

7 Claims, No Drawings

SYNTHESIS OF SUBSTITUTED 1-ARALKYL-1H-V-TRIAZOLES

This invention relates to a process of preparing aralkyl-v-triazoles.

The aralkyl-v-triazoles which are prepared by the process of the present invention are those represented by the formulas

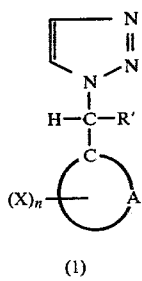 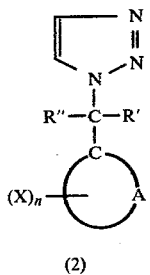

(1)    (2)

where A together with the carbon atom shown form a phenyl or naphthyl radical; R' and R" each independently represent a lower alkyl radical, aralkyl radical or aralkyl radical substituted with a base stable substituent on the ring of the aralkyl radical; X represents a base stable substituent; and n is 0 to 3 with the proviso that if the below described steps (c) and (d) of the present process are to be carried out said base stable substituents must also be oxidation stable.

The products prepared by the process of this invention can be used as fungicides and miticides.

In accordance with the present invention the compounds represented by formulas (1) and (2) above are prepared by a process comprising:

(a) reacting a compound represented by the formula

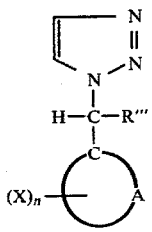

(3)

with an alkylating agent in the presence of a base and a solvent to produce a product containing at least 1 compound represented by the formulas:

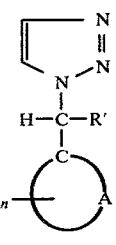 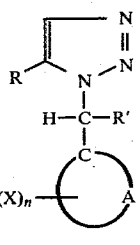 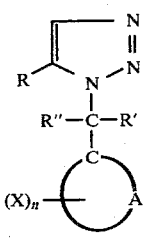

(4)    (5)    (6)

(b) separating the product of step (a) into the individual compounds prepared in step (a);

(c) reacting a compound represented by formulas (5) or (6) with an oxidizing agent to produce a product represented by the following formulas (7) and (8)

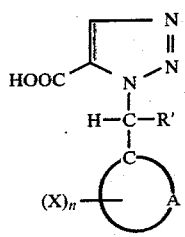 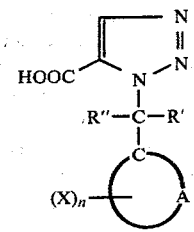

(7)    (8)

respectively; and (d) decarboxylating the product of step (c) by heating to remove the carboxyl group from the 5-position of the triazole ring, wherein A together with the carbon atoms shown suitably form a phenyl or naphthyl radical; R represents a lower alkyl radical; R' and R" each independently represents a lower alkyl radical, aralkyl radical or aralkyl radical substituted with a base stable substituent on the ring of the aralkyl radical; R''' represents a hydrogen atom, lower alkyl radical, aralkyl radical or an aralkyl radical substituted with a base stable substituent on the ring of the aralkyl radical; X represents a base stable substituent; and n is 0 to 3 with the proviso that if the above described process steps (c) and (d) carried out said base stable substituents are also oxidation stable.

Included within the term "base stable substituent" as used herein are all such art recognized substituents including a halogen atom, a lower alkyl radical, a lower alkoxy radical and a nitro radical (—NO$_2$). Such substituents are also oxidation stable except for "a lower alkyl radical". Therefore, if steps (c) and (d) of the present process are to be carried out R', R" or R''' is not an aralkyl radical substituted with a lower alkyl radical nor is X a lower alkyl radical.

In a preferred embodiment of the present invention A together with the carbon atom shown in the above formulas form a phenyl group; R', R" and R''' each independently represent a lower alkyl radical, aralkyl radical, a lower alkoxy substituted aralkyl radical where the substitution is on the ring of the aralkyl radical, a halogen substituted aralkyl radical where the substitution is on the ring of the aralkyl radical or a nitro-substituted aralkyl radical where the substitution is on the ring of the aralkyl radical, and R''' also represents a hydrogen atom; and X represents a halogen atom, lower alkoxy radical or a nitro radical.

In a further preferred embodiment of the present invention compounds made by the process of the present invention represented by formulas (1) and (2) above are those where A together with the carbon atom shown form a phenyl group; R' and R" and R''' each independently represent a lower alkyl radical having 1 to 6 carbon atoms, a phenylalkyl radical having 7 to 12 carbons atoms, a mono-, di-, or tri-lower alkoxy (C$_1$ to C$_4$) substituted phenylalkyl radical having 7 to 12 carbon atoms where the substitution is on the phenyl ring, a mono-, di-, or tri-halogen substituted phenylalkyl radical having 7 to 12 carbon atoms where the substitution is on the phenyl ring, or a mono-, di-, or tri-nitro-substituted phenylalkyl having 7 to 12 carbon atoms where the substitution is on the phenyl ring, and R''' also represents a hydrogen atom; X represents a halogen atom, lower alkoxy radical having 1 to 4 carbon atoms or a nitro radical and n is 0 or 1.

In another embodiment of this invention a compound represented by formula (3) above where R''' is hydrogen is reacted in step (a) to produce a product represented by formula (4) above where A together with the carbon atom shown from a phenyl radical; R' independently represents a lower alkyl radical having 1 to 6 carbon atoms, a phenylalkyl radical having 7 to 12 carbon atoms, a mono-, di- to tri-lower alkyl ($C_1$ to $C_4$) substituted phenylalkyl radical having 7 to 12 carbon atoms where the substitution is on the phenyl ring, a mono-, di- or tri-lower alkoxy ($C_1$ to $C_4$) substituted phenylalkyl radical having 7 to 12 carbon atoms where the substitution is on the phenyl ring, a mono-, di- or tri-halogen substituted phenylalkyl radical having 7 to 12 carbon atoms where the substitution is on the phenyl ring, or a mono-, di- or tri-nitro-substitution phenylalkyl having 7 to 12 carbon atoms where the substitution is on the phenyl ring; X represents a halogen atom, a lower alkyl radical having 1 to 4 carbon atoms, a lower alkoxy radical having 1 to 4 carbon atoms or a nitro radical; and n is 1.

Where the term halogen is used herein it is used to define that well-known group of halogens having an atomic weight of no greater than 127 and represented by fluorine, chlorine, bromine and iodine.

The alkylating agents used in step (a) of the present process can be suitably any one of this well-known group of compounds including alkyl, aralkyl or substituted aralkyl halides. Examples of such alkylating compounds include methyl iodide, ethyl bromide, benzyl bromide and 2-iodopropane. These halide reactants or alkylating agents used to prepare the products of the present process above can readily be prepared by known methods. For example, they can readily be prepared from their corresponding alcohol compound by reaction with an excess of a suitable agent, such as thionyl chloride or phosphorus halide, such as $PCl_3$ and $PCl_5$. However, it is considered the halide reactants needed to prepare the subject compounds are commercially available.

The base used in step (a) of the present process can be any suitable alkali metal amide or organo-lithium compound, for example lithium amide, sodium amide, lithium diisopropylamide or n-butyl lithium.

Among the suitable solvents that can be used in step (a) of the present process are diethyl ether, tetrahydrofuran, dioxane and liquid ammonia.

In accordance with the present process if it is desired to prepare a monoalkylated intermediate or final product represented by formula (4) above, a mole ratio of alkylating agent, to base, to suitable substituted v-triazole represented by formula (3) where R''' is hydrogen of 1 to 3 moles alkylating agent to 1 to 3 moles of base to 1 mole of suitable v-triazole is recommended. However, a mole ratio of 1:1:1 respectively is found to be preferred.

If a dialkylated intermediate represented by (5) above is desired a mole ratio of 3 to 10 moles alkylating agent, to 3 to 10 moles base to one mole substituted v-triazole represented by formula (3), where R''' is hydrogen or lower alkyl, aralkyl or substituted aralkyl, is recommended. However, a ratio of 10:10:1 respectively is preferred. Use of the present process with the ratio of reactants specified in this paragraph will yield a reaction product that also contains a small amount of compound represented by formula (4) above.

When a trialkylated intermediate represented by formula (6) above is desired a mole ratio of 10 to 15 moles alkylating agent, to 10 to 15 moles base, to 1 mole substituted v-triazole represented by formula (3), where R''' is hydrogen or lower alkyl, aralkyl or substituted aralkyl is recommended. However, results indicate that a mole ratio of 15:15:1 respectively is preferred. Using this method and mole ratios of reactants indicated in this paragraph will also produce a small amount of the compound represented by formula (5) above and trace amount of the compound represented by formula (4) above.

The triazole products of the process of this invention can be used to treat growing plants (including trees, shrubs and flowering plants) prior to or after infestation with fungi and/or mites, by applying the triazoles to the plants. The triazole products of the present process can be applied in any of the convenient forms generally used for pesticide formulations, such as powders, suspensions, emulsions or solutions, containing 0.05% to 0.2% w/w of the subject v-triazoles.

The powders or dusts are prepared by admixing a suitable quantity of the active triazole compound with finely divided inert solids such as talc, natural clays, diatomaceous earth, fuller's earth or flours such as walnut shell. Liquid compositions are prepared by admixing one or more of the triazole compounds of the present process with a suitable inert liquid diluent. If desired the present triazole compounds can be directly dissolved in a suitable solvent, such as denatured alcohol, and sprayed on a plant in need of such treatment. Alternatively, the present triazole compounds can be blended with a suitable surface active agent such as TWEEN ® 40 polyoxyethylene (20) sorbitan monopalmitate to enable the triazole compounds to be dispersed in water to prepare a spray for application to the plants in need of treatment for fungus and/or mites. For example, a 0.1% w/w water dispersion can be prepared by first mixing 1.0 gram 1-[2-(2-chlorophenyl) propyl]-5-methyl-1H-v-triazole with 3.0 grams of TWEEN ® 40 polyoxyethylene (20) sorbitan monopalmitate. The resulting blend is then dispersed by stirring in sufficient water to make 1,000 grams of aqueous spray.

In accordance with the present invention the products of the present process, as well as the intermediates therefor, can be separated by known conventional techniques such as column chromatography, high pressure liquid chromatography, distillation and crystallization procedures as illustrated in the following methods and examples.

The substituted v-triazole reactants used in step (a) of the present process can be suitably prepared in accordance with following Method I followed by the process steps illustrated in following Examples 1 to 5 or by following Method II.

Method I

Preparation of 1,2,3-Triazole

Step 1—Preparation of Hydrazoic Acid: According to the method of H. Wolff, Organic Reactions, Vol. III, p. 327 (1946).

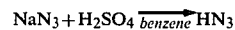

$$NaN_3 + H_2SO_4 \xrightarrow{benzene} HN_3$$

Step 2—Preparation of 4-Carboxy-1,2,3-Triazole: According to the method of C. Pedersen, Acta Chemica Scandinavica, 13, 888 (1959).

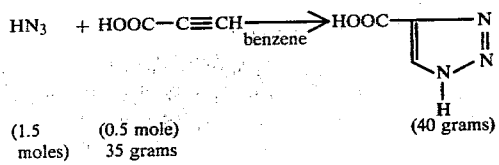

Step 3—Preparation of 1,2,3-Triazole: According to the method of C. Pedersen, Acta Chemica Scandinavica, 13, 888 (1959).

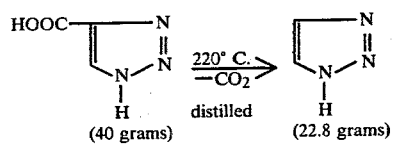

Alternatively, v-triazole can be prepared by the thermal decarboxylation of 4,5-dicarboxy-1H-v-triazole (a known compound) by the method disclosed by Wiley et al. in Journal of Organic Chemistry, 21, 190 (1956).

METHOD II

Preparation of Substituted-1H-v-Triazoles and 1,4,5-Tri-Substituted-1H-v-Triazoles The azide reactants required can be prepared by the reaction of an appropriate halide reactant, for example, a suitable aralkyl halide or substituted aralkyl halide, with sodium azide in aqueous ethanol according to Moulin's method (F. Moulin, Helvetica Chimica Acta, 35, 175 (1952)). The resulting azide, for example, an aralkyl azide, is then reacted with acetylene dicarboxylic acid in acetone to give 1-aralkyl-4,5-dicarboxy-1H-v-triazole. Thermal decarboxylation of the 1-aralkyl-4,5-dicarboxy-1H-v-triazole is then carried out to give 1-aralkyl-1H-v-triazole (R. H. Wiley, V. F. Hussing and J. Moffat, Journal of Organic Chemistry, 21, 190 (1959)). The generalized synthetic sequence can be represented in the following manner:

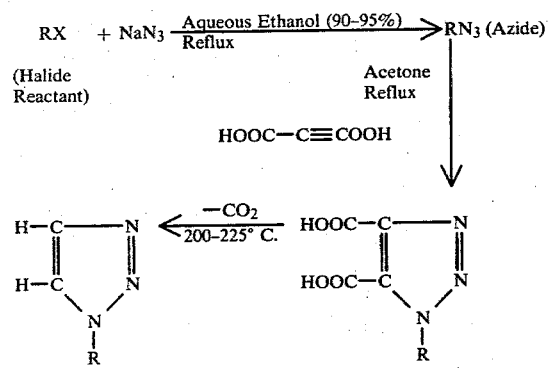

R in the above synthetic sequence suitably represents an aralkyl radical or substituted aralkyl radical.

EXAMPLE 1

1-(4-Fluorobenzyl)-v-Triazole

To a stirred solution of 8.1 grams (0.15 mole) of sodium methoxide in 50 ml of methanol, 10.35 grams (0.15 mole) of 1H-v-triazole were added in one portion and p-fluorobenzyl chloride (21.74 grams, 0.15 mole) was added in 10 minutes. The reaction mixture was stirred at 25° C. for 24 hours. Thn the reaction mixture was filtered through a sintered glass funnel to remove sodium chloride. The filtrate was evaporated to dryness and an additional amount of NaCl was filtered off. The product, a yellow liquid, was fractionated under reduced pressure. A fraction, which distilled at 100°–110° C./0.1 mm Hg as a colorless liquid, was identified as the 1-(4-fluorobenzyl)-1H-v-triazole.

Analysis calculated for $C_9H_8N_3F_1$: C, 60.99%; H, 4.55%; N, 23.71%; F, 10.73%. Found: C, 61.01%; H, 4.80%; N, 23.63%; F, 10.92%.

EXAMPLE 2

1-(3-Methylbenzyl)-1H-v-Triazole

To a stirred solution of 7.1 grams (0.13 mole) of sodium methoxide in 50 ml of methanol, 9.1 grams (0.13 mole) of 1H-v-triazole were added in one portion. 3-methylbenzyl chloride, 19.0 grams (0.13 mole), was added to this solution in one portion. The reaction mixture was stirred at room temperature for 24 hours. The reaction mixture was filtered through a sintered glass funnel to remove sodium chloride. The filtrate was evaporated to dryness under aspirator vacuum at 40° C. The residue was distilled under reduced pressure to remove low boiling fractions. The pot residue was triturated with methylene chloride and solid was filtered off. Filtrate was evaporated to dryness and the residue was recrystallized from a mixture of benzene-petroleum ether (b.p. 60°–110° C.). The solid was filtered, washed with petroleum ether, and dried. 1(3-methylbenzyl)-1H-v-triazole having a melting point of 66.5°–67° C. was obtained.

EXAMPLE 3

1(4-Methoxybenzyl)-1H-v-Triazole

To a stirred solution of sodium methoxide 8.1 grams (0.15 mole) in 60 ml methanol, 10.4 grams (0.15 mole) of 1H-v-triazole were added in one portion and then 4-methoxy-benzyl chloride, 24.4 grams (0.15 mole), was added in one portion. The reaction mixture was stirred at room temperature for 24 hours. The reaction mixture was filtered through a sintered glass funnel to remove sodium chloride. The filtrate was evaporated to dryness on a steam bath. The residue was vacuum distilled and a fraction boiling at 39°–45° C./0.1 mm Hg was then column chromatographed on Silica Gel G column packed with benzene. Benzene: diethyl ether (1:1) was used for elution. The fractions containing the product were evaporated and the residue recrystallized three times from absolute ethanol to yield 1-(4-methoxybenzyl)-1H-v-triazole, having a melting point of 89°–91° C.

Analysis calculated for $C_{10}H_{11}N_3O$ (m.w. 189.2): C, 63.47%; H, 5.86%; N, 22.21%. Found: C, 63.14%; H, 6.05%; N, 22.19%.

EXAMPLE 4

1(3-Nitrobenzyl)-1H-v-Triazole

To a stirred solution of 6.9 grams (0.3 mole) sodium metal reacted in 150 ml methanol, 20.7 grams (0.3 mole) of 1H-v-triazole were added in one portion. 3-Nitrobenzyl chloride, 56.6 grams (0.3 mole), was added to this solution in one portion at room temperature. Reaction mixture was stirred at room temperature for 24 hours. The reaction mixture was filtered through a sintered glass funnel to remove sodium chloride. The filtrate was evaporated to dryness under aspirator vacuum at 40° C.

The residue was extracted with chloroform and chloroform layer was washed twice with water. The organic layer was dried over $Na_2SO_4$, filtered, and filtrate evaporated to dryness. The residue was triturated with diethyl ether, filtered, and washed with hexane. The solid was sublimed at 130°–135° C./0.1 mm Hg and the initial sublimate was washed off until solid began to sublime. The sublimed solid was recrystallized from 25 ml boiling methanol to yield a pale yellow solid, having a melting point of 97°–97.5° C., identified as 1-(3-nitrobenzyl)-1H-v-triazole.

Analysis calculated for $C_9H_8N_4O_2$ (m.w. 204.2): C, 52.94%; H, 3.95%; N, 27.44%. Found: C, 52.97%; H, 4.23%; N, 27.50%.

EXAMPLE 5

1-(2-Iodobenzyl)-1H-v-Triazole

To a stirred solution of 2.1 grams (0.09 mole) sodium metal reacted in 100 ml methanol, 6.1 grams (0.09 mole) of 1H-v-triazole were added in one portion. 2-Iodobenzyl bromide, 26.4 grams (0.09 mole), was added gradually to this solution at room temperature. Methanol (100 ml) was added to aid solubility of the halide. Reaction mixture was stirred at room temperature for 24 hours; then the reaction mixture was evaporated to dryness under aspirator vacuum at 40° C. The residue was extracted with chloroform and sodium bromide was filtered off. The filtrate was dried over $MgSO_4$ and chloroform was stripped off under aspirator vacuum at 40° C. Residual oil was extracted with diethyl ether and ether layer was decanted off. A solid was precipitated when a small amount of hexane was added to the ethereal solution. This yellow solid was sublimed under vacuum to give 1-(2-iodobenzyl)-1H-v-triazole, having a melting point of 62.5°–63.5° C.

Analysis calculated for $C_9H_8N_3I$ (m.w. 285.1): C, 37.92%; H, 2.83%; N, 14.74%; I, 44.51%. Found: C, 37.86%; H, 2.80%; N, 14.82%; I, 44.59%.

The following described METHOD III more particularly illustrates the process of the present invention.

METHOD III

Step (a)

A suitable 1-aralkyl-1H-v-triazole or substituted aralkyl-1H-v-triazole with or without an asymmetric carbon atom depending on the product desired is reacted with an appropriate alkylating agent, for example methyl iodide or dimethyl sulfate, in a suitable solvent, for example liquid ammonia in the presence of sodium amide under reflux at atmospheric pressure. The reaction mixture is then gently warmed to drive off the liquid ammonia. At the same time the volume is kept constant by the addition of diethyl ether. The product mixture is then isolated by the addition of $H_2O$ followed by the separation of the organic phase. The solvent is then removed by flash distillation.

Step (b)

The resulting product mixture of Step (a) above is then separated by column chromatography using a suitable adsorbent, for example Silica Gel G, and the column is developed using a suitable solvent system, for example 50/50 hexane:diethyl ether. The isolated 1-(α-alkyl aralkyl)-5-alkyl-1H-v-triazole and 1-(α,α'dialkyl aralkyl)-5-alkyl-1H-v-triazole are further purified by recrystallization from a suitable solvent system, for example hexane/diethyl ether in the case of solids or distillation in the case of liquid products.

Step (c) (1)

The 1-(α-alkyl aralkyl)-5-alkyl-1H-v-triazole isolated in Step 1 is reacted with an aqueous solution of any known suitable oxidizing agent, for example potassium permanganate, in the presence of a suitable base, for examople sodium carbonate, by heating the mixture under reflux at atmospheric pressure. The mixture is allowed to cool and is then filtered and the filtrate is adjusted to pH 2 with a suitable acid, for example hydrochloric acid, to precipitate the product 1-(α-alkyl aralkyl)-5-carboxy-1H-v-triazole.

Step (c)(2)

The 1-(α,α'-dialkyl aralkyl)-5-alkyl-1H-v-triazole isolated in Step 1 is reacted with an aqueous solution of an oxidizing agent, for example potassium permanganate, in the presence of a suitable base, for example sodium carbonate, by heating the mixture under reflux at atmospheric pressure. The mixture is allowed to cool and then filtered and the filtrate is adjusted to pH 2 with a suitable acid, for example hydrochloric acid, to precipitate the product 1-(α,α'-dialkyl aralkyl)-5-carboxy-1H-v-triazole.

Step (d)

Decarboxylation is carried out to remove the carboxyl group from the 5-position of the triazole ring of the products of Steps (c)(1) and (c)(2).

The following Examples are further illustrative of the above-described process to prepare the subject compounds.

EXAMPLE 6

(1-[1-(2-chlorophenyl)propyl]-1H-v-triazole)

To a suspension of 3.01 grams (0.077 mole) of $NaNH_2$ in 250 ml of refluxing liquid $NH_3$ was added in one portion 15 grams (0.077 mole) of 1-[1-(2-chlorophenyl)methyl]-1H-v-triazole. After 15 minutes of stirring, 8.44 grams (0.077 mole) of ethyl bromide was added dropwise over ½ hour. The mixture was stirred an additional 3 hours under reflux. The liquid ammonia was boiled off as diethyl ether was added to maintain a constant volume. The mixture was treated with 20 ml of 95% ethanol followed by 200 ml of $H_2O$. The mixture was extracted with three 200 ml portions of diethyl ether. The organic phase was taken to dryness on the rotary evaporator to yield 20grams of crude product which was chromatographed on Silica Gel G. Elution with diethyl ether gave the desired product (1-[1-(2-chlorophenyl)propyl]-1H-v-triazole) in 50% yield. NMR, MS and IR were identical to those of an authentic sample prepared by an alternate route.

EXAMPLE 7

1-[1-(2-Chlorophenyl-2-propyl]-5-methyl-1H-v-triazole 1-[1-(2-Chlorophenyl)-ethyl]-1H-v-triazole 19.5 grams (0.5 mole) of freshly prepared sodium amide is suspended in 150 ml of anhydrous diethyl ether. At 20° C. the mixture is treated with 10 grams (0.5 mole) of 1-[1-(2-chlorophenyl)methyl]-1H-v-triazole in one portion. After 5 minutes of stirring, 71.9 grams (0.05 mole) of methyl iodide is added dropwise to the mixture over 30 minutes. After the completion of the addition of methyl iodide the mixture is heated under reflux for an additional hour. The mixture is allowed to cool to room temperature and the excess sodium amide is destroyed by the addition of 20 ml of 95% ethanol, followed with 50 ml of water. The mixture is then treated with an additional 250 ml of water and is extracted with three 250 ml portions of diethyl ether. The combined organic phase is dried over anhydrous magnesium sulfate. The drying agent is filtered off and washed with diethyl ether. The combined filtrates are taken to dryness on a rotary evaporator under water aspirator vacuum and the residue is column chromatographed on Silica Gel G, which is developed with 50/50 hexane:ether. The 1-[2-(2-chlorophenyl)propyl]-5-methyl-1H-v-triazole is isolated and characterized.

Analysis calculated for $C_{12}H_{14}N_3Cl$ (MW-235.72): C, 61.15%; H, 5.99%; N, 17.83%; Cl, 15.04. Found: C, 61.23%; H, 5.74; N, 17.92%; Cl, 14.89%.

The side product 1-[1-(2-chlorophenyl)ethyl]-5-methyl-1H-v-triazole product is obtained and has a melting point of 69°–70° C. Analysis calculated for $C_{11}H_{12}N_3Cl$ (MW=221.69): C, 59.60%; H, 5.46%; N, 18.95%; Cl, 15.99%. Found: C, 59.56%; H, 5.68%; N, 19.09%; Cl, 16.00%.

A suspension of 8.3 grams (0.035 mole) of 1-[2-(2-chlorophenyl)propyl]-5-methyl-1H-v-triazole obtained above, 4.0 grams (0.037 mole) of sodium carbonate and 600 ml of water is heated to reflux. 32 grams (0.2 mole) of potassium permanganate is added in portions over ½ hour. The mixture is heated under reflux for an additional 2½ hours. The mixture is allowed to cool to room temperature and the excess potassium permanganate is destroyed by the addition of oxalic acid. The destruction of potassium permanganate is complete when the purple color discharges. The solids are filtered off and washed with water.

The combined filtrates are adjusted to pH 2 with concentrated hydrochloric acid to yield a white product which is filtered off and dried in the vacuum oven. This product 1-[2-(2-chlorophenyl)propyl]-5-carboxy-1H-v-triazole is used in the next step with no further purification.

(Analysis calculated for $C_{12}H_{12}N_3ClO_2$ (MW-265.70): C, 54.25% H, 4.55%, N, 15.81% Cl, 13.31%. Found: C, 54.48%; H, 4.75% N, 15.69%, Cl, 13.31%.

The product 1-[2-(2-chlorophenyl)propyl]-5-carboxy-1H-v-triazole is thermally decarboxylated in an oil bath by heating at 170°–180° C. for 15 minutes. The residue is fractionally distilled at reduced pressure to yield 1-[2-(2-chlorophenyl)propyl]-1H-v-triazole, BP=139°–140° C. at 0.01 mm.

Analysis calculated for $C_{11}H_{12}N_3Cl$ (MW-221.69): C, 59.60%; H, 5.46%, N, 18.95%; Cl, 15.99%. Found: C, 59.67%; H, 5.52% N, 18.97%; Cl, 15.94%.

EXAMPLE 8

1-[1-(2-chlorophenyl)-2-methylpropyl]-1H-v-triazole

To a stirred suspension of 3.9 grams (0.1 mole) of $NaNH_2$ in 150 ml of refluxing liquid ammonia was added in one portion 20.0 grams (0.1 mole) of 1-[(2-chlorophenyl)methyl]-1H-v-triazole. The mixture was stirred for 15 minutes then 5.1 grams (0.1 mole) of 2-iodopropane, dissolved in 50 ml of anhydrous diethyl ether, was added dropwise over ½ hour. The mixture was stirred under reflux for an additional 2 hours. The ammonia was then allowed to boil off while the volume of the mixture was maintained constant by the addition of diethyl ether. The mixture was then treated with 25 ml of 95% ethanol followed by 250 ml $H_2O$. The mixture was extracted with three 200 ml portions of diethyl ether. The combined organic phases were dried over anhydrous $MsSO_4$. The drying agent was filtered off, washed with ether and the filtrate taken to dryness. The crude product was chromatographed on Silica Gel G and the product eluted with 50-50 hexane ether. The product was recrystallized from 3:1 diethyl ether/hexane to give 1-[1-(2-chlorophenyl)-2-methylpropyl]-1H-v-triazole m.p. 67°–68° C.

Analysis calculated for $C_{12}H_{14}N_3Cl$ (M.W.-235.71); C, 61.15%; H, 5.99%, N, 17,83%; Cl, 15.04%. Found: C, 61.19%; H, 5.73%; N, 17.74%; Cl, 15.22%.

EXAMPLE 9

1-[1-(4-chlorophenyl)ethyl]-1H-v-triazole

To a stirred suspension of 1.95 grams (0.05 mole) of $NaNH_2$ in 100 ml of refluxing liquid ammonia was added 10 grams (0.05 mole) of 1-[1-(4-chlorophenyl)methyl]-1H-v-triazole in one portion. The mixture was stirred for 15 minutes then 7.1 grams (0.05 mole) of methyl iodide dissolved in 25 ml of anhydrous diethyl ether was added dropwise. The mixture was stirred an additional 2½ hours under reflux. The ammonia was then allowed to boil off and the volume of the mixture was maintained constant by the addition of ether. The mixture was treated with 25 ml of 95% ethanol followed by 25 ml $H_2O$. The mixture was extracted with two 100 ml portions of diethyl ether. The combined organic layers are washed successively with saturated sodium chloride and water, then dried over anhydrous $MgSO_4$. The drying agent was filtered off, washed with diethyl ether and the combined filtrates taken to dryness in vacuo. The residue was chromatographed on Silica Gel G eluted with 50/50 hexane/diethyl ether. The product is vacuum sublimed to yield 1-[1-(4-chlorophenyl)ethyl]-1H-v-triazole m.p. 55°–56° C.

Analysis calculated for $C_{10}H_{10}N_3Cl$ (MW-207.66): C, 57.84%; H, 4.85%; N, 20.23%; Cl, 17.07%. Found: C, 58.14%; H, 5.06%; N, 20.07%; Cl, 17.24%.

EXAMPLE 10

1-[1-(2-chlorophenyl)-2-phenylethyl]-1H-v-triazole

To a suspension of 2.3 grams (0.05mole) of $NaNH_2$ in 200 ml of refluxing liquid ammonia was added in one portion 10 grams (0.05 mole) of 1-[1-(2-chlorophenyl)-methyl]-1H-v-triazole and the mixture was stirred for ½ hour. 8.8 grams (0.05 mole) of benzyl bromide was added dropwise over 20 minutes. After the addition the mixture was stirred an additional 2½ hours at reflux. The mixture was treated with 25 ml of 95% ethanol followed by 100 ml of water then extracted with three 200 ml portions of diethyl ether. The combined organic phases were washed twice with water then dried over anhydrous $MgSO_4$. The drying agent was filtered off and washed with diethyl ether. The combined filtrates were then taken to dryness in vacuo. The residue was chromatographed on Silica Gel G, and eluted with 50/50 hexane/diethyl ether. The solid product was recrystallized from hexane/ether to give 1-[1-(2-chlorophenyl)-2-phenylethyl]-1H-v-triazole—m.p.—84°–86° C.

Analysis calculated for $C_{16}H_{14}N_3Cl$ (MW—283.63): C, 67.73%; H, 4.97%; N, 14.83%; Cl, 12.49%. Found: C, 67.73%; H, 5.17%; N, 14.98%; Cl, 12.81%.

EXAMPLE 11

1-[1-(2-fluorophenyl)-2-methylpropyl]-1H-v-triazole

To a suspension of 1.56 grams (0.04 mole) of NaNH$_2$ in 200 ml of refluxing liquid ammonia was added in one portion 7.3 grams (0.04 mole) of 1-[1-(2-fluorophenyl)-methyl]-1H-v-triazole. The mixture was stirred for ½ hour, then 7.0 grams (0.04 mole) of 2-iodopropane was added dropwise over 10 minutes. The mixture was stirred an additional 2½ hours at reflux, then treated with 25 ml of 95% ethanol followed by 100 ml of H$_2$O. The mixture was extracted with two 200 ml portions of diethyl ether. The combined organic phase was washed with saturated sodium chloride followed by H$_2$O, then dried over anhydrous MgSO$_4$. The drying agent was filtered off, washed with diethyl ether and the filtrate taken to dryness. The residue was chromatographed on Silica Gel G and developed by gradient elution with hexane/diethyl ether. The product was finally purified by vacuum sublimation to give 1-[1-(2-fluorophenyl)-2-methylpropyl]-1H-v-triazole m.p.—63°-4° C.

Analysis calculated for C$_{12}$H$_{14}$N$_3$F (MW—219.3): C, 65.75%; H, 6.44%; N, 19.16%; F, 8.66%. Found: C, 65.80%; H, 6.28%; N, 19.22%; F, 8.49%.

EXAMPLE 12

1-[1-(2-chlorophenyl)propyl]-5-methyl-1H-v-triazole

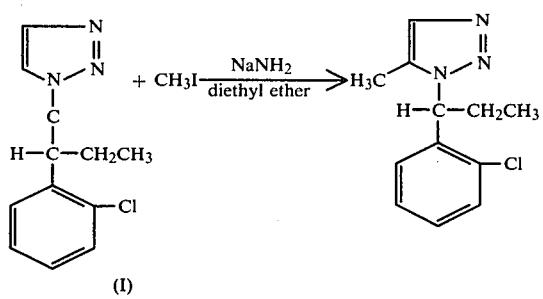

(I)

0.4 Mole of NaNH$_2$ was suspended in 250 ml of anhydrous diethyl ether. 9 grams (0.04 mole) of (I) was added in one portion at ambient temperature and the color of the mixture rapidly became brown. After ten additional minutes 56.8 grams (0.4 mole) of methyl iodide was added dropwise over ½ hour. The mixture was then heated under reflux overnight. The mixture had become slate gray in color. Heat was discontinued and the mixture was cautiously treated with 30 ml ethanol followed by 100 ml water. Then about one-half of the resulting mixture was transferred to a separatory funnel and 250 ml of water was added to dissolve all solids. The mixture was then extracted with two 300 ml portions of diethyl ether and the etheral layer was dried over anhydrous MgSO$_4$ and taken to dryness to yield 11 grams of a brown oil. The resulting oil was flash distilled at 0.01 mm to yield 9 grams of a pale straw liquid product. By NMR and mass spectroscopy the product was identified as consisting principally of 1-[1-(2-chlorophenyl) propyl]-5-methyl-1H-v-triazole.

It will be observed that the compounds of this invention may contain at least one asymmetric carbon atom. The racemic form of such a compound may, therefore, be resolved into two optically active forms. It is to be understood that this invention encompasses the racemic form of the compounds described hereinabove, and in addition any optically-active enantiomeric form which possesses the useful properties of the compound of the invention, as hereafter defined, it being a matter of common general knowledge how to resolve a racemate into its optically-active isomers and determine the biological properties thereof.

What is claimed is:

1. A process of preparing compounds represented by formulas

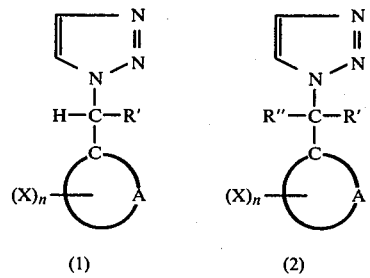

(1)  (2)

comprising:

(a) reacting a compound represented by the formula

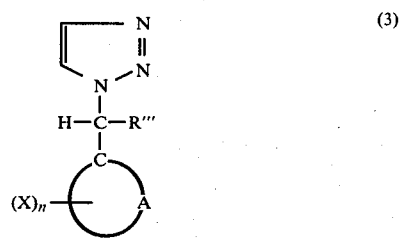

(3)

with an alkylating agent in the presence of a base and a solvent to produce a product containing at least one compound represented by the formulas

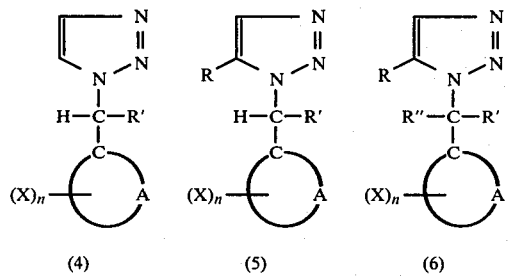

(4)  (5)  (6)

(b) separating the product of step (a) into the individual compounds prepared in step (a);

(c) reacting a compound represented by formulas (5) or (6) with an oxidizing agent to produce a product represented by the following formulas (7) and (8)

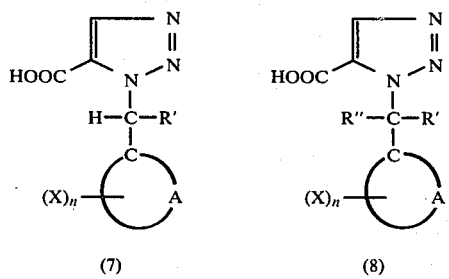

(7)  (8)

respectively; and (d) decarboxylating the product of step (c) by heating to form compounds represented by formulas (1) and (2), wherein A together with the carbon atom shown form a phenyl radical; R', R" and R'" each independently represent a lower alkyl radical having 1 to 6 carbon atoms, a phenylalkyl radical having 7 to 12 carbon atoms, a mono-, di- or tri-lower alkoxy ($C_1$ to $C_4$) substituted phenylalkyl radical having 7 to 12 carbon atoms where the substitution is on the phenyl ring, a mono-, di- or tri-halogen substituted phenylalkyl radical having 7 to 12 carbon atoms where the substitution is on the phenyl ring, or a mono-, di- or tri-nitro substituted phenylalkyl having 7 to 12 carbon atoms where the substitution is on the phenyl ring and R'" also represents a hydrogen atom; X represents a halogen atom, lower alkoxy radical having 1 to 4 carbon atoms or a nitro radical, and n is 0 or 1.

2. A process of claim 1 wherein R'" is hydrogen and the product of step (a) is represented by the formulas

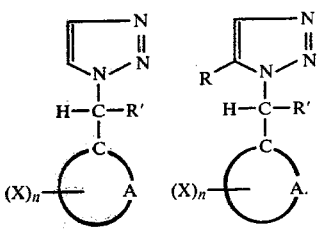

3. A process of claim 1 wherein the product of step (a) is represented by the formulas

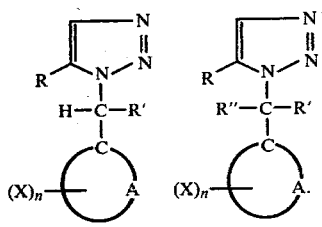

4. A process of claim 1 wherein the triazole reactant and alkylating agent of step (a) are 1-[1-(2-chlorophenyl)methyl]-1H-v-triazole and ethyl bromide respectively.

5. A process of claim 1 wherein the triazole reactant and oxidizing agent of step (c) are 1-[2-(2-chlorophenyl)propyl]-5-methyl-1H-v-triazole and potassium permanganate respectively.

6. A process of claim 5 wherein the product of step (c) is 1-[2-(2-chlorophenyl)propyl]-5-carboxy-1H-v-triazole.

7. A process of claim 6 wherein the product of step (d) is 1-[2-(2-chlorophenyl)propyl]-1H-v-triazole.

* * * * *

UNITED STATES PATENT AND TRADEMARK OFFICE
CERTIFICATE OF CORRECTION

PATENT NO. : 4,227,004
DATED : October 7, 1980
INVENTOR(S) : Richard Alan Wildonger It is certified that error appears in the above-identified patent and that said Letters Patent are hereby corrected as shown below:

Column 5 - Method II - Line 48 - the line in the formula reading -HOOC-C≡COOH-should read "HOOC-C≡C-COOH"

*Signed and Sealed this*

*Seventeenth* Day of *February 1981*

[SEAL]

*Attest:*

RENE D. TEGTMEYER

*Attesting Officer*  *Acting Commissioner of Patents and Trademarks*